(12) United States Patent
Krusic et al.

(10) Patent No.: US 8,785,013 B2
(45) Date of Patent: *Jul. 22, 2014

(54) COMPOSITIONS CONTAINING MODIFIED FULLERENES

(75) Inventors: Paul J. Krusic, Wilmington, DE (US); Helen S. M. Lu, Wallingford, PA (US); Zhen-Yu Yang, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 592 days.

This patent is subject to a terminal disclaimer.

(21) Appl. No.: 11/205,455

(22) Filed: Aug. 17, 2005

(65) Prior Publication Data

US 2006/0073370 A1   Apr. 6, 2006

Related U.S. Application Data

(60) Provisional application No. 60/603,089, filed on Aug. 20, 2004.

(51) Int. Cl.
*H01M 2/36* (2006.01)

(52) U.S. Cl.
USPC .............. 429/11; 252/62.2; 521/27; 429/492; 429/494; 429/516; 429/524; 429/535

(58) Field of Classification Search
USPC ........... 429/33; 423/445 B; 252/62.2; 521/27; 526/27; 562/1
See application file for complete search history.

(56) References Cited

U.S. PATENT DOCUMENTS

| | | | |
|---|---|---|---|
| 3,282,875 A | 11/1966 | Connolly et al. | |
| 3,641,104 A | 2/1972 | Anderson et al. | |
| 3,664,915 A | 5/1972 | Gore | |
| 3,953,566 A | 4/1976 | Gore | |
| 3,962,153 A | 6/1976 | Gore | |
| 4,187,390 A | 2/1980 | Gore | |
| 4,216,073 A | 8/1980 | Goldstein | |
| 4,358,545 A | 11/1982 | Ezzell et al. | |
| 4,940,525 A | 7/1990 | Ezzell et al. | |
| 5,277,996 A * | 1/1994 | Marchetti et al. | 429/535 |
| 5,300,203 A | 4/1994 | Smalley | |
| 5,316,636 A | 5/1994 | Bunshah et al. | |
| 5,354,926 A | 10/1994 | Fagan | |
| 5,382,718 A * | 1/1995 | Bekiarian et al. | 570/129 |
| 5,382,719 A * | 1/1995 | Fagan | 570/144 |
| 5,416,243 A * | 5/1995 | Bekiarian et al. | 568/660 |
| 5,422,411 A * | 6/1995 | Wei et al. | 526/243 |
| 5,635,041 A * | 6/1997 | Bahar et al. | 204/282 |
| 5,919,583 A | 7/1999 | Grod et al. | |
| 5,922,537 A * | 7/1999 | Ewart et al. | 435/6 |
| 5,958,523 A | 9/1999 | Bradic et al. | |
| 5,962,746 A | 10/1999 | Diffendall et al. | |
| 5,985,232 A | 11/1999 | Howard et al. | |
| 6,448,412 B1 | 9/2002 | Murphy et al. | |
| 6,495,290 B1 * | 12/2002 | Hinokuma et al. | 429/231.8 |
| 6,645,455 B2 | 11/2003 | Margrave et al. | |
| 6,706,431 B2 * | 3/2004 | Kawamura et al. | 429/13 |
| 6,890,676 B2 | 5/2005 | Nuber | |
| 7,195,834 B2 * | 3/2007 | Srinivas | 429/33 |
| 2002/0142206 A1 | 10/2002 | Hinokuma | |
| 2003/0148161 A1 * | 8/2003 | Nuber et al. | 429/33 |
| 2004/0044139 A1 | 3/2004 | Grootaert | |
| 2004/0057896 A1 | 3/2004 | Kronholm et al. | |
| 2004/0109816 A1 * | 6/2004 | Srinivas et al. | 423/449.2 |
| 2004/0115501 A1 | 6/2004 | Hinokuma | |
| 2004/0169165 A1 | 9/2004 | Srinivas | |
| 2005/0009039 A1 | 1/2005 | Jagota et al. | |
| 2006/0093885 A1 | 5/2006 | Krusic | |
| 2007/0293693 A1 | 12/2007 | Krusic et al. | |

FOREIGN PATENT DOCUMENTS

| | | | | |
|---|---|---|---|---|
| EP | 1 353 392 A1 | 10/2003 | | |
| JP | 2002063918 A | 2/2002 | | |
| JP | 2002216792 A | 8/2002 | | |
| JP | 2004014120 A | 1/2004 | | |
| WO | WO 92/04279 | 3/1992 | | |
| WO | WO 00/24709 | * 5/2000 | ............ | C07C 309/81 |
| WO | WO 00/77057 | * 12/2000 | ............ | C08F 128/00 |
| WO | WO 00/77057 A2 | 12/2000 | | |
| WO | WO 2004/112099 A2 | 12/2004 | | |

OTHER PUBLICATIONS

M. Hudlicky, Reactions of Organic Fluorine Compounds, Chemistry of Organic Fluorine Compounds, 2$^{nd}$ Ed Ellis Horwood Ltd., 1976, pp. 450-463.
U.S. Appl. No. 10/716,347, filed Nov. 18, 2003, Anand Jagota et al.
Satoshi Matsui et al; A Novel Reaction of [60]Fullerence, A Formal [2+2] Cycloaddition with Aryloxy- and Alkoxyketenes, *Tetrahedron Letters* 40 (1999) 899-902, Elsevier, New York.

* cited by examiner

Primary Examiner — Brandon Fetterolf
Assistant Examiner — Blaine G Doletski

(57) ABSTRACT

Compositions containing modified fullerenes and their use, for example, as films for membranes in electrode assemblies for electrochemical cells and fuel cells such as fuel cells are described.

22 Claims, No Drawings

COMPOSITIONS CONTAINING MODIFIED FULLERENES

This application claims the benefit of U.S. Provisional Application No. 60/603,089, filed on Aug. 20, 2004, which is incorporated in its entirety as a part hereof for all purposes.

FIELD OF THE INVENTION

This invention relates to compositions containing modified fullerenes and their use as films or in other fabricated forms in the field of electronics in devices such as membranes, electrode assemblies and electrocatalysts as found in electrochemical cells and fuel cells.

BACKGROUND OF THE INVENTION

Electrochemical cells are devices that convert fuel and oxidant to electrical energy. Electrochemical cells generally include an anode electrode and a cathode electrode separated by an electrolyte. A variety of known electrochemical cells fall within a category of cells often referred to as solid polymer electrolyte (SPE) cells. An SPE cell typically employs a membrane of an ion exchange polymer that serves as a physical separator between the anode and cathode while also serving as an electrolyte. SPE cells can be operated as electrolytic cells for the production of electrochemical products or they may be operated as fuel cells for the production of electrical energy. The most well known fuel cells are those which operate with gaseous fuels such as hydrogen and with a gaseous oxidant, usually pure oxygen or oxygen from air, and those fuel cells using direct feed organic fuels such as methanol.

In some SPE cells including many fuel cells, a cation exchange membrane is employed, and protons are transported across the membrane as the cell is operated. Such cells are often referred to as proton exchange membrane (PEM) cells. For example, in a cell employing the hydrogen/oxygen couple, hydrogen molecules (fuel) at the anode are oxidized donating electrons to the anode, while at the cathode the oxygen (oxidant) is reduced accepting electrons from the cathode. The H+ ions (protons) formed at the anode migrate through the membrane to the cathode and combine with oxygen to form water. In many fuel cells, the anode and/or cathode are provided by forming a layer of electrically conductive, catalytically active particles, usually also including a polymeric binder, on the proton exchange membrane, and the resulting structure (sometimes also including current collectors) is referred to as a membrane electrode assembly or MEA.

Membranes made from a cation exchange polymer such as perfluorinated sulfonic acid polymer have been found to be particularly useful for MEAs and electrochemical cells due to good conductivity and good chemical and thermal resistance which provide long service life before replacement. However, increased proton conductivity is desired for some applications, particularly for fuel cells that operate at high current densities.

A need thus remains in the art for compositions having properties that make them desirable for use as films from which membranes may be fabricated, which compositions also have desirable properties in other applications in the filed of electronics.

SUMMARY OF THE INVENTION

One embodiment of this invention is a composition that includes a polymer and one or more cyclofluoroalkylated fullerene compounds of Formula I

(I)

wherein:
$R^1$ and $R^2$ are independently H, F, Cl, Br, CN, a branched or straight chain alkyl, alkylether, alkoxy, alkoxyether, fluoroalkyl, fluoroalkylether, fluoroalkoxy, fluoroalkoxyether, aryl, aryloxy, fluoro-aryl, or fluoroaryloxy groups; optionally substituted with one or more of H, Cl, Br, carbinol, carboxylic acid ester, carboxylic acid halide, sulfonyl fluoride, or carbonitrile groups;
$R^3$ is F or a branched or straight chain fluoroalkyl or fluoroalkylether group;
$R^4$ is a branched or straight chain hydrocarbon alkyl or alkyl ether or aromatic hydrocarbon group;
$R^5$ is independently one or more selected from H, F and Cl;
n is an integer from 0 to about 470;
w is an integer from 1 to 16+(n/2) for n=an even integer, or from 1 to 16+[(n+1)/2] for n=an odd integer;
x is an integer from 0 to about 24+n;
y is an integer from 0 to about 24+n; and
z is an integer from 0 to about 35+n.

Preferably n is an integer from 0 to 5; $R^1$ and $R^2$ are independently H, F, Cl or CN; $R^3$ is a perfluoroalkyl or perfluoroalkylether; $R^4$ is a hydrocarbon alkyl or alkyl ether; $R^5$ is H; x, y and z are 0 to 3+n; and w is 1 to 15.

Another embodiment of this invention is a film prepared from this composition, as well as articles made from such film. Another embodiment of this invention is a membrane prepared from the above described composition.

In a further embodiment of this invention, the polymeric component of a composition may contain cation exchange groups. In such event, a further embodiment is provided in which a film prepared from such composition is used to make a membrane. The invention is thus also further directed to a membrane and electrode assembly, an electrochemical cell or a fuel cell that contains such a membrane.

Another embodiment of this invention is a composition that includes a modified fullerene as described above and an electrocatalytic metal.

A further embodiment of this invention is an anode electrocatalyst that includes one or more noble metals and one or more cyclofluoroalkylated fullerene compounds as described above. The invention is thus also further directed to an electrochemical cell or a fuel cell that contains such an anode electrocatalyst.

DETAILED DESCRIPTION OF THE INVENTION

A composition of this invention contains a polymer and one or more cyclofluoroalkylated fullerene compounds as described herein. These compositions can be made into films by any film forming method as typically used in the art such as solvent casting on a heated surface, or thermal pressing of an extrudate. A film prepared from a composition of this invention can be incorporated into a polymer membrane suitable for use in a fuel cell and other electrochemical cells, demonstrating good ionic conductivity and solubility with the polymer.

The present invention is thus directed in part to a membrane made from a composition hereof having fullerenes with fluorinated functionalities. The membrane may be made from a film formed from a composition as used herein, but may also be made by other means that do not involve a step of film formation. These films and membranes that contain functionalized fullerene materials are suitable for use in fuel cells, batteries, electrolysis cells, ion exchange membranes, sensors, electrochemical capacitors, and modified electrodes. The invention is also directed, however, to membranes that additionally contain electrically-conductive, catalytically-active particles, and to electrode assemblies, electrochemical and fuel cells comprising such a membrane.

Fullerenes

The functionalized fullerenes in the composition, film and membrane composite of the present invention include one or more cyclofluoroalkylated fullerene compounds, preferably cycloperfluoroalkylated fullerene compounds, as described by Formula I $$(C_{60+2n})(CF_2CR^1R^2)_w R^3_x R^4_y R^5_z \quad (I)$$

wherein:

$R^1$ and $R^2$ are independently H, F, Cl, Br, CN, a branched or straight chain alkyl, alkylether, alkoxy, alkoxyether, fluoroalkyl, fluoroalkylether, fluoroalkoxy, fluoroalkoxyether, aryl, aryloxy, fluoro-aryl, or fluoroaryloxy groups; optionally substituted with one or more of H, Cl, Br, carbinol, carboxylic acid ester, carboxylic acid halide, sulfonyl fluoride, or carbonitrile groups;

$R^3$ is F or a branched or straight chain fluoroalkyl or fluoroalkylether group;

$R^4$ is a branched or straight chain hydrocarbon alkyl or alkyl ether or aromatic hydrocarbon group;

$R^5$ is independently one or more selected from H, F and Cl;

n is an integer from 0 to about 470;

w is an integer from 1 to 16+(n/2) for n=an even integer, or from 1 to 16+[(n+1)/2] for n=an odd integer;

x is an integer from 0 to about 24+n;

y is an integer from 0 to about 24+n; and z is an integer from 0 to about 35+n.

In various alternative embodiments of the functionalized fullerene described above n may be an integer from 0 to 5;

$R^1$ and $R^2$ may be independently H, F, Cl or CN;

$R^3$ may be a perfluoroalkyl or perfluoroalkylether group;

$R^4$ may be a hydrocarbon alkyl or alkyl ether group;

$R^5$ may be H; x, y and z are 0 to 3+n; and/or w may be 1 to 15.

In various other alternative embodiments of the functionalized fullerene described above, n may be 0 to 5, $R^5$ may be H and z may be 0 to 2;

$R^1$ may be F and $R^2$ may be F;

$R^1$ may be F and $R^2$ may be $OCF_3$;

$R^1$ may be F and $R^2$ may be $CF_3$; and/or $R^1$ may be F and $R^2$ may be Cl.

In various other alternative embodiments, the polymer may comprise a highly fluorinated carbon backbone with a side chain represented by the formula $$-(OCF_2CFR^7)_a-OCF_2CFR^8SO_3X$$

wherein $R^7$ and $R^8$ are independently selected from F, Cl or a perfluorinated alkyl group having 1 to 10 carbon atoms; a=0, 1 or 2; and X may be H, an alkali metal or $NH_4$.

Preparation of these fullerenes can be performed in any manner, one of which is described in U.S. Pat. No. 5,382,718, which is incorporated in its entirety as a part hereof for all purposes. The thermolysis process for cycloaddition of fluoroalkenes with themselves and other alkenes to form fluorocyclobutane rings is generally known in the art, as for example from Hudlicky, M., *Chemistry of Organic Fluorine Compounds*, 2nd ed Ellis Horwood Ltd, pp 450-463, 1976. The thermolysis process to prepare the cyclofluoroalkylated fullerene compounds of Formula I, or mixtures of more than one thereof, in accordance with this invention involves heating one or more fullerene compounds of Formula II $$(C_{60+2n})R^3_x R^4_y R^5_z \quad (II)$$

with fluoroalkene compounds of Formula III $$CF_2CR^1R^2 \quad (III)$$

either as pure fluoroalkenes (e.g. tetrafluoroethylene) or as mixtures of fluoroalkenes, from about 100° C. to about 350° C., preferably from about 150° C. to about 250° C., and most preferably from about 150° C. to about 200° C. without, or preferably with, an organic or halocarbon solvent, such as 1,2,4-trichlorobenzene, under a pressure of about 0 to about $1.1 \times 10^7$ Pascals (0 to about 1600 psi) of the fluoroalkene, for a period of from about 1 hour to about 96 hours, preferably about 1 hour to about 18 hours. Typically the reaction is carried out in a sealed stainless steel pressure vessel, with a pressure gauge for determining the pressure, and an internal thermocouple for measuring temperature.

The product from the above reactions is generally isolated by first evaporating or distilling off under reduced pressure all or most of the excess compounds of Formula III and any solvent. The product is redissolved in an organic or halocarbon solvent such as tetrahydrofuran, 1,1,2-trichlorotrifluoroethane, or hexafluorobenzene and filtered. The solvent is then evaporated under reduced pressure to yield a mixture comprised of cyclofluoroalkylated fullerene compounds of Formula I. Addition of an organic or haloorganic solvent such as hexane allows for collection of the product by filtration if it is insoluble, or cooling to –78° C. will precipitate the product which can be then be collected.

The functional groups on the fullerenes of this invention may themselves be further functionalized by, for example, conversion to salts, hydrolysis or oxidation. One such example is the hydrolysis of the carboxylic acid halide or sulfonyl fluoride of $R^1$ and $R^2$.

Unlike most fullerenes known in the art, the mixtures of this invention are surprisingly soluble in a variety of organic liquids, particularly halocarbon liquids such as chlorofluorocarbons, e.g. 1,1,2-trichlorotrifluoroethane and hexafluorobenzene.

Membrane

A membrane in accordance with this invention is made from a composition of a modified fullerene and a polymer having cation exchange groups that can transport protons across the membrane. The cation exchange groups are preferably selected from the group consisting of sulfonate, carboxylate, phosphonate, imide, sulfonimide and sulfonamide groups. Various known cation exchange polymers can be used, including polymers and copolymers of trifluoroethylene, tetrafluoroethylene, styrene-divinyl benzene, α,β,β-trifluorstyrene and the like, in which cation exchange groups have been introduced. α,β,β-trifluorstyrene polymers useful for the practice of the invention are disclosed in U.S. Pat. No. 5,422,411, which is incorporated as a part hereof, and may be more particularly described by the following structural formula

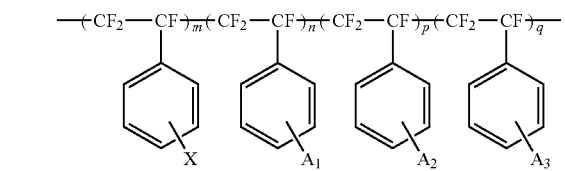

in which at least two of m, n, p and q are integers greater than zero;

$A_1$, $A_2$ and $A_3$ are selected from the group consisting of alkyls, halogens, $C_yF_{2y+1}$ where y is an integer greater than zero, O—R (where R is selected from the group consisting of alkyls, perfluoroalkyls and aryls),
CF=CF$_2$,
CN,
NO$_2$ and
OH; and
X is selected from the group consisting of
SO$_3$H,
PO$_2$H$_2$,
PO$_3$H$_2$,
CH$_2$PO$_3$H$_2$,
COOH,
OSO$_3$H,
OPO$_3$H$_2$,
OArSO$_3$H where Ar is an aromatic,
NR$_3$+ (where R is selected from the group consisting of alkyls, perfluoroalkyls and aryls), and
CH$_2$NR$_3$+ (where R is selected from the group consisting of alkyls, perfluoroalkyls and aryls).

The A$_1$, A$_2$, A$_3$ and X substituents may be located in the ortho, meta and/or para positions. The copolymer may also be binary, ternary or quaternary.

The polymeric composition in which m and n are integers greater than zero, p and q are both zero, A$_1$ is fluorine or CF$_3$, and X is SO$_3$H, may be suitably formed into a membrane, and may be preferably employed as an ion-exchange membrane, most preferably as a cation exchange membrane in an electrochemical fuel cell.

In another embodiment, the polymeric composition may include:

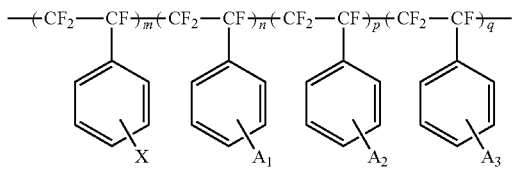

where m is an integer greater than zero and at least one of n, p and q is an integer greater than zero; A$_1$, A$_2$ and A$_3$ are selected from the group consisting of alkyls, halogens, C$_y$F$_{2y+1}$ where y is an integer greater than zero, O—R (where R is selected from the group consisting of alkyls, perfluoroalkyls and aryls), CF=CF$_2$, CN, NO$_2$ and OH; and X is selected from the group consisting of SO$_3$H, PO$_3$H$_2$, CH$_2$PO$_3$H$_2$, COOH, OSO$_3$H, OPO$_3$H2, OArSO$_3$H where Ar is an aromatic, NR$_3$+ (where R is selected from the group consisting of alkyls, perfluoroalkyls and aryls) and CH$_2$NR$_3$+ (where R is selected from the group consisting of alkyls, perfluoroalkyls and aryls).

In yet another embodiment, the group from which A$_1$, A$_2$ and A$_3$ are selected further consists of SO$_3$H, PO$_3$H$_2$, CH$_2$PO$_3$H$_2$, COOH, OSO$_3$H, OPO$_3$H$_2$, OArSO$_3$H where Ar is an aromatic, NR$_3$+ (where R is selected from the group consisting of alkyls, perfluoroalkyls and aryls) and CH$_2$NR$_3$+ (where R is selected from the group consisting of alkyls, perfluoroalkyls and aryls); wherein at least one of A$_1$, A$_2$ and A$_3$ is selected from the group consisting of SO$_3$H, PO$_3$H$_2$, CH$_2$PO$_3$H$_2$, COOH, OSO$_3$H, OPO$_3$H$_2$, OArSO$_3$H where Ar is an aromatic, NR$_3$+ (where R is selected from the group consisting of alkyls, perfluoroalkyls and aryls) and CH$_2$NR$_3$+ (where R is selected from the group consisting of alkyls, perfluoroalkyls and aryls); and wherein A$_1$, A$_2$ and A$_3$, when present, are each group members other than X.

In a preferred form of the invention, the polymer comprises a polymer backbone and recurring side chains attached to the backbone with the side chains carrying the cation exchange groups. For example, copolymers of a first fluorinated vinyl monomer, and a second fluorinated vinyl monomer having a side cation exchange group or a cation exchange group precursor, can be used. A suitable side group for this purpose is a sulfonyl fluoride group (—SO$_2$F), which can be subsequently hydrolyzed to a sulfonic acid group. Possible first monomers include tetrafluoroethylene, hexafluoropropylene, vinyl fluoride, vinylidine fluoride, trifluorethylene, chlorotrifluoroethylene, perfluoro(alkyl vinyl ether), and mixtures thereof. Possible second monomers include a variety of fluorinated vinyl ethers with cation exchange groups or precursor groups.

Preferably, in a polymer as used in a composition from which a membrane is prepared in this invention, the polymer has a polymer backbone that is highly fluorinated, and the ion exchange groups are sulfonate groups. The term "sulfonate groups" is intended to refer either to sulfonic acid groups or alkali metal or ammonium salts of sulfonic acid groups. "Highly fluorinated" means that at least 90% of the total number of positions for halogen and hydrogen atoms contain fluorine atoms. Most preferably, the polymer backbone is perfluorinated. It is also preferable for the side chains to be highly fluorinated and, most preferably, the side chains are perfluorinated.

In various other alternative embodiments, the cation exchange groups of the polymer are selected from the group consisting of sulfonate, carboxylate, phosphonate, imide, sulfonimide and sulfonamide; or the polymer may be highly fluorinated polymer with sulfonate cation exchange groups.

A class of preferred polymers for such use in the present invention includes a highly fluorinated, most preferably perfluorinated, carbon backbone, and a side chain represented by Formula IV

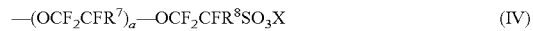

wherein R$^7$ and R$^8$ are each independently selected from F, Cl or a perfluorinated alkyl group having 1 to 10 carbon atoms, a=0, 1 or 2, and X is H, an alkali metal, or NH$_4$. The preferred polymers include, for example, polymers as disclosed in U.S. Pat. Nos. 4,358,545 and 4,940,525, which are incorporated as a part hereof. Most preferably, the polymer comprises a perfluorocarbon backbone, and the side chain is represented by Formula V

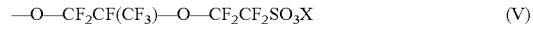

wherein X is H, an alkali metal or NH$_4$. Polymers of this type are disclosed in U.S. Pat. No. 3,282,875, which is incorporated as part hereof.

The equivalent weight of the cation exchange polymer can be varied as desired for the particular application. Equivalent weight is defined herein to be the weight of the polymer in sulfonic acid form required to neutralize one equivalent of NaOH. In the case where the polymer comprises a perfluorocarbon backbone and the side chain is the salt of —O—CF$_2$—CF(CF$_3$)—O—CF$_2$—CF$_2$—SO$_3$X, the equivalent weight preferably is 800-1500, and most preferably 900-1200. The equivalent weight of polymers that may be similar to those disclosed in U.S. Pat. Nos. 4,358,545 and 4,940,525 is preferably somewhat lower, e.g. 600-1300.

In the manufacture of a membrane from a composition containing a polymer that has a highly fluorinated polymer backbone and sulfonate ion-exchange groups, the membrane is typically formed with the polymer in its sulfonyl fluoride form since it is thermoplastic in this form, and conventional techniques for making films from thermoplastic polymer can be used. Alternatively, the polymer may be in another thermoplastic form in which —SO$_2$X groups, where X is CH$_3$, CO$_2$ or a quaternary amine, are present. Solution film casting techniques using suitable solvents for the particular polymer can also be used if desired.

If the polymer contained in a film or a membrane is in sulfonyl fluoride form, it can be converted to the sulfonate form (sometimes referred to as ionic form) by hydrolysis using methods known in the art. For example, a polymer may be hydrolyzed to convert it to the sodium sulfonate form by immersing a film or membrane in 25% by weight NaOH for about 16 hours at a temperature of about 90° C. followed by rinsing twice in deionized 90° C. water using about 30 to about 60 minutes per rinse. Another method employs an aqueous solution of 6-20% of an alkali metal hydroxide and 5-40% polar organic solvent, such as dimethyl sulfoxide, with a contact time of at least 5 minutes at 50-100° C. followed by rinsing for 10 minutes. After hydrolyzing, the polymer can be converted if desired to another ionic form by immersion of a film or membrane in a bath containing a 1% salt solution containing the desired cation, or to the acid form by contact with an acid and rinsing. For fuel cell use, the polymer in the membrane is usually in the sulfonic acid form.

A membrane may be prepared as a composite from films of the compositions used in this invention where the films are obtained by any means. One method is to prepare a composition by dispersing a functionalized fullerene material in solution or dispersion with a selected cation exchange polymer in a suitable solvent such as an alcohol, DMF, ketone, water or mixed solvents. The dispersion is then cast on a glass plate or on another surface, and the solvents are then removed to give a thin film. In some cases, heating the film to above 150° C. is desirable to improve the mechanical and other properties.

Another method is to form a film for use in a membrane by melt extrusion. A composition of a polymer and the functionalized fullerene material is prepared by intimate mixing by grinding and/or milling under appropriate conditions. The resulting materials can be pressed or extruded into thin films thermally.

If desired, a membrane may be prepared from a film obtained by laminating together two films that are prepared from compositions of this invention in which the respective polymers, such as two highly fluorinated polymers, have different ion-exchange groups and/or different ion-exchange capacities. In an alternative embodiment, a membrane may be prepared from a film that is obtained by co-extruding a film from compositions of this invention in which the respective polymers, such as two highly fluorinated polymers, have different ion-exchange groups and/or different ion-exchange capacities. In addition, a membrane may be prepared from a film obtained from a composition containing a blend of two or more polymers, such as two or more highly fluorinated polymers, having different ion-exchange groups and/or different ion-exchange capacities. A film may be formed into a membrane, for example, by pressing a film onto, or applying a film as a decal to, a suitable substrate.

A membrane may optionally include a porous support to improve mechanical properties or decrease cost. The porous support of the membrane may be made from a wide range of components. Suitable materials for a support include a hydrocarbon such as a polyolefin, e.g. polyethylene, polypropylene, polybutylene and copolymers of those materials, and the like. Perhalogenated polymers such as polychlorotrifluoroethylene may also be used as the support. For resistance to thermal and chemical degradation, the support preferably is made of a highly fluorinated polymer, most preferably perfluorinated polymer.

For example, the polymer for the porous support can be a microporous film of polytetrafluoroethylene (PTFE) or a copolymer of tetrafluoroethylene with a monomer such as

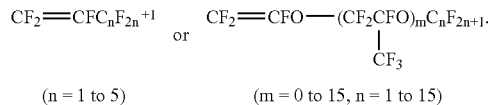

(n = 1 to 5)   (m = 0 to 15, n = 1 to 15)

Examples of microporous PTFE films and sheeting suitable for use as a support layer are described in U.S. Pat. No. 3,664,915, which discloses uniaxially stretched film having at least 40% voids; and in U.S. Pat. Nos. 3,953,566, 3,962,153 and 4,187,390, which disclose porous PTFE films having at least 70% voids. Alternately, the porous support may be a fabric made from fibers of the polymers discussed above woven using various weaves such as the plain weave, basket weave, leno weave or the like.

A membrane can be made using a porous support by coating a cation exchange polymer on the support so that the coating is on the outside surfaces as well as being distributed through the internal pores of the support. This may be accomplished by impregnating the porous support with a solution/dispersion of a composition of a cation exchange polymer, or cation exchange polymer precursor, using a solvent that is not harmful to the polymer or the support under the impregnation conditions such that a thin, even coating of the cation exchange polymer is formed on the support. For example, for applying a coating of perfluorinated sulfonic acid polymer to a microporous PTFE support, a 1-10 weight percent solution/dispersion of the polymer in water mixed with sufficient amount of a polar organic solvent can be used. The support, with the solution/dispersion impregnated therein, is dried to form the membrane. If desired, thin films of the ion exchange polymer can be laminated to one or both sides of the impregnated porous support to prevent bulk flow through the membrane, which can occur if large pores remain in the membrane after impregnation. Alternatively, a composition of the functionalized carbon material, cation exchange polymer and, optionally a catalytic metal, may be formed as an ink, and sprayed on printed onto a support or substrate.

The thickness of the membrane can be varied as desired for a particular electrochemical cell application. Typically, the thickness of the membrane is generally less than about 250 µm, preferably in the range of about 25 µm to about 150 µm.

Membrane Electrode Assembly

A membrane of the present invention can optionally comprise an electrode formed from electrically conductive, catalytically active particles, preferably particles of transition metals, including Group VIII metals such as Ru, Rh and Pt. These particles can be in the form of a catalyst "ink", either mixed with the fullerene materials or formed as a separate layer. The catalyst layers may be made from particles or materials known to be electrically conductive and/or catalytically active. The catalyst layer may be formed as a film of a polymer that serves as a binder for the catalyst particles. The binder polymer can be a hydrophobic polymer, a hydrophilic polymer or a mixture of such polymers. Preferably, the binder polymer is a polymer having cation exchange groups, and most preferably is the same polymer as in the membrane.

The catalyst layers are preferably formed using an "ink", i.e. a solution of the binder polymer and the catalyst particles, and optionally the fullerene materials of the present invention, that is in turn used to apply a coating to the membrane. The viscosity of the ink is preferably controlled in a range of 1 to $10^2$ poises, especially about $10^2$ poises, before printing. The viscosity can be controlled by (i) selecting particle sizes, (ii) adjusting the relative content in the composition of the catalytically active particles and binder, (iii) adjusting the water content (if present), or (iv) by incorporating a viscosity regulating agent such as carboxymethyl cellulose, methyl cellulose, hydroxyethyl cellulose, and cellulose and polyethyleneglycol, polyvinyl alcohol, polyvinyl pyrrolidone, sodium polyacrylate or polymethyl vinyl ether.

The area of the membrane to be coated with the ink may be the entire area or only a selected portion of the surface thereof. The catalyst ink may be deposited upon the surface of the membrane by any suitable technique including spreading it with a knife or blade, brushing, pouring, metering bars, spraying and the like. If desired, the coatings are built up to a desired thickness by repetitive application. Areas on the surface of the membrane that require no catalyst materials can be masked, or other means can be taken to prevent the deposition of the catalyst material on such areas. The desired loading of catalyst upon the membrane can be predetermined, and the specific amount of catalyst material can be deposited upon the surface of the membrane so that no excess catalyst is applied. The catalyst particles are preferably deposited upon the surface of a membrane in a range from about 0.2 mg/cm$^2$ to about 20 mg/cm$^2$.

Electrocatalysts

A functionalized fullerene composition of the present invention can also be used in the preparation of anode electrocatalysts used in electrochemical cells. A composition of a modified fullerene hereof and an electrocatalytic metal is incorporated into an anode electrocatalyst. The electrocatalyst can include one or more noble metal catalysts, with the optional additional presence of other metals. Metals useful as electrocatalysts are discussed in Ullmann's Encyclopedia of Industrial Chemistry, Fuel Cells, 2002, DOI: 10.1002/14356007.a12_055, and Kirk-Othmer Encyclopedia of Chemical Technology, Fuel Cells, 2002, DOI: 10.1002/0471238961.0621051211091415.a01.pub2; which disclosures are incorporated as a part hereof for all purposes.

Preferably the noble metal electrocatalysts are Group VIII metals including platinum or platinum-ruthenium electrocatalysts. These electrocatalysts are typically dispersed on high surface area supports with noble metal concentrations between 5 to 40 weight percent. For industrial applications, support materials include, for example, carbon, carbonaceous materials, aluminum oxide, silicon oxide and ceramic.

The term "noble metal" as used herein means elemental metals that are highly resistant to corrosion and/or oxidation. Noble metals include, for example, ruthenium, rhodium, palladium, silver, rhenium, osmium, iridium, platinum and gold. Preferable noble metals include platinum, ruthenium and mixtures thereof.

The electrocatalyst can be applied to the surface of the SPE that faces the anode, to the surface of the anode facing the SPE, or to both surfaces. In an alternative embodiment, the electrocatalyst is coated on the surfaces of both electrodes facing the SPE, both surfaces of the SPE, or a combination thereof. In accordance with another aspect of this invention, the substrate comprises a SPE. In accordance with a further aspect, the substrate comprises an electrode, preferably an anode.

Known electrocatalyst coating techniques can be used, and will produce a wide variety of applied layers of essentially any thickness ranging from very thick, e.g. 20 µm or more, to very thin, e.g. 1 µm or less.

Electrochemical Cells

The membranes and anode electrocatalysts in accordance with the invention are advantageously employed in electrode assemblies for electrochemical cells, particularly fuel cells, and in battery systems, particularly lithium batteries.

An electrochemical cell may contain an anode compartment containing an anode, a cathode compartment containing a cathode, and a membrane serving as a separator and electrolyte between said anode and cathode compartments. A fuel cell may contain an anode compartment containing an anode, a cathode compartment containing a cathode and a membrane serving as a separator and electrolyte between said anode and cathode compartments.

A further description of electrode assemblies and their use in electrochemical cells can be found in U.S. Pat. No. 5,919,583, which is incorporated in its entirety as a part hereof for all purposes.

Where the composition of this invention is stated or described as comprising, including, containing, having, being composed of or being constituted by certain components, it is to be understood, unless the statement or description explicitly provides to the contrary, that one or more components in addition to those explicitly stated or described may be present in the composition. In an alternative embodiment, however, the composition of this invention may be stated or described as consisting essentially of certain components, in which embodiment components that would materially alter the principle of operation or the distinguishing characteristics of the composition are not present therein. In a further alternative embodiment, the composition of this invention may be stated or described as consisting of certain components, in which embodiment components other than impurities are not present therein.

Where the indefinite article "a" or "an" is used with respect to a statement or description of the presence of a component in the composition of this invention, it is to be understood, unless the statement or description explicitly provides to the contrary, that the use of such indefinite article does not limit the presence of the component in the composition to one in number.

Where an apparatus of this invention is stated or described as comprising, including, containing, having, being composed of or being constituted by certain components, it is to be understood, unless the statement or description explicitly provides to the contrary, that one or more components other than those explicitly stated or described may be present in the apparatus. In an alternative embodiment, however, the apparatus of this invention may be stated or described as consisting essentially of certain components, in which embodiment components that would materially alter the principle of operation or the distinguishing characteristics of the apparatus would not be present therein. In a further alternative embodiment, the apparatus of this invention may be stated or described as consisting of certain components, in which embodiment components other than those as stated would not be present therein.

The term "alkyl" as employed herein includes both straight and branched chain radicals, for example methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof. The chain may be linear or cyclic, saturated or unsaturated, containing, for example, double and triple bonds. The alkyl chain may be interrupted or substituted with, for example, one or more halogen, oxygen, hydroxy, silyl, amino, or other acceptable substituents.

The term "acyl" as used herein refers to carbonyl groups of the formula —COR wherein R may be any suitable substituent such as, for example, alkyl, aryl, aralkyl, halogen; substituted or unsubstituted thiol; unsubstituted or substituted amino, unsubstituted or substituted oxygen, hydroxy, or hydrogen.

The term "aryl" as employed herein refers to monocyclic, bicyclic or tricyclic aromatic groups containing from 6 to 14 carbons in the ring portion, such as phenyl, naphthyl, substituted phenyl, or substituted naphthyl, wherein the substituent on either the phenyl or naphthyl may be for example C 1-4 alkyl, halogen, C 1-4 alkoxy, hydroxy or nitro.

The term "aralkyl" as used herein refers to alkyl groups as discussed above having an aryl substituent, such as benzyl, p-nitrobenzyl, phenylethyl, diphenylmethyl, and triphenylmethyl.

The term "aromatic or non-aromatic ring" as used herein includes 5-8 membered aromatic and non-aromatic rings uninterrupted or interrupted with one or more heteroatom, for example O, S, SO, SO 2, and N, or the ring may be unsubstituted or substituted with, for example, halogen, alkyl, acyl, hydroxy, aryl, and amino, said heteroatom and substituent may also be substituted with, for example, alkyl, acyl, aryl, or aralkyl.

The term "linear or cyclic" when used herein includes, for example, a linear chain which may optionally be interrupted by an aromatic or non-aromatic ring. Cyclic chain includes, for example, an aromatic or non-aromatic ring which may be connected to, for example, a carbon chain which either precedes or follows the ring.

What is claimed is:

1. A composition comprising a mixture of (a) a polymer that consists essentially of
   (i) one or more monomers selected from the group consisting of tetrafluoroethylene, hexafluoropropylene, vinyl fluoride, vinylidine fluoride, trifluorethylene, chlorotrifluoroethylene, perfluoro(alkyl vinyl ether); and
   (ii) one or more monomers selected from the group consisting of (1) fluorinated vinyl ethers comprising perfluorinated side chains that comprise cation exchange groups selected from the members of the group consisting of carboxylate, phosphonate, imide, sulfonamide and sulfonimide groups; and (2) monomers comprising a side chain represented by the structure of the following Formula (IV)

—(OCF$_2$CFR$^7$)$_a$—OCF$_2$CFR$^8$SO$_3$X  (IV)

wherein R$^7$ and R$^8$ are each independently selected from F or a perfluorinated alkyl group having 1 to 10 carbon atoms, a = 0, 1 or 2, and X is H, an alkali metal, or NH$_4$; and
   (b) one or more cyclofluoroalkylated fullerene compounds of Formula I (C$_{60+2n}$)(CF$_2$CR$^1$R$^2$)$_w$R$^3_x$R$^4_y$R$^5_z$  (I)

wherein:
   R$^1$ is F;
   R$^2$ is OCF$_3$, CF$_3$, or Cl;
   R$^3$ is a perfluoroalkyl or perfluoroalkylether group;
   R$^4$ is a hydrocarbon alkyl or alkyl ether group;
   R$^5$ is H;
   n is an integer from 0 to 5;
   w is an integer from 1 to 15;
   x is an integer from 0 to 3+n;
   y is an integer from 0 to 3+n; and
   z is an integer from 0 to 3+n.

2. A film comprising the composition of claim 1.

3. A membrane comprising the composition of claim 1.

4. The membrane as recited in claim 3 wherein, in the cyclofluoroalkylated fullerene compound, R$^2$ is OCF$_3$.

5. The membrane as recited in claim 3 wherein, in the cyclofluoroalkylated fullerene compound, R$^2$ is CF$_3$.

6. The membrane as recited in claim 3 wherein, in the cyclofluoroalkylated fullerene compound, R$^2$ is Cl.

7. The membrane of claim 3 wherein the polymer is highly fluorinated.

8. The membrane of claim 3 wherein the polymer is perfluorinated.

9. The membrane of claim 3 wherein the cation exchange groups are selected from the members of the group consisting of sulfonamide and sulfonimide groups.

10. A membrane and electrode assembly comprising the membrane of claim 3.

11. The membrane and electrode assembly of claim 10 wherein the electrode comprises a layer of electrically-conductive, catalytically-active particles.

12. The membrane and electrode assembly of claim 11 wherein the catalytically-active particles comprise one or more noble metals.

13. An electrochemical cell comprising an anode, a cathode and a membrane according to claim 3.

14. An electrochemical cell according to claim 13 that further comprises an anode compartment and a cathode compartment, wherein the membrane further comprises an electrolyte and separates the anode compartment from the cathode compartment.

15. A fuel cell comprising an anode, a cathode and a membrane according to claim 3.

16. A fuel cell according to claim 15 that further comprises an anode compartment and a cathode compartment, wherein the membrane further comprises an electrolyte and separates the anode compartment from the cathode compartment.

17. The membrane of claim 3 which further comprises a support prepared from a hydrocarbon polymer.

18. The membrane of claim 17 wherein the support comprises a highly fluorinated polymer or a perfluorinated polymer.

19. The membrane of claim 17 wherein the support comprises polytetrafluoroethylene (PTFE) or a copolymer of tetrafluoroethylene with a monomer selected from the group consisting of

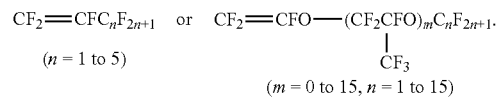

20. The composition as recited in claim 1 wherein, in the cyclofluoroalkylated fullerene compound, and R$^2$ is OCF$_3$.

21. The composition as recited in claim 1 wherein, in the cyclofluoroalkylated fullerene compound, and R$^2$ is CF$_3$.

22. The composition as recited in claim 1 wherein, in the cyclofluoroalkylated fullerene compound, R$^2$ is Cl.

* * * * *